(12) United States Patent
Huang

(10) Patent No.: US 8,704,165 B2
(45) Date of Patent: Apr. 22, 2014

(54) GENE DETECTING METHODS WITHOUT USING PCR

(76) Inventor: Lequn Huang, Jiangsu (CN)

( * ) Notice: Subject to any disclaimer, the term of this patent is extended or adjusted under 35 U.S.C. 154(b) by 0 days.

(21) Appl. No.: 13/635,879

(22) PCT Filed: Feb. 17, 2011

(86) PCT No.: PCT/CN2011/071044
§ 371 (c)(1),
(2), (4) Date: Sep. 18, 2012

(87) PCT Pub. No.: WO2011/113313
PCT Pub. Date: Sep. 22, 2011

(65) Prior Publication Data
US 2013/0140451 A1 Jun. 6, 2013

(30) Foreign Application Priority Data
Mar. 19, 2010 (CN) .......................... 2010 1 0147160

(51) Int. Cl.
*H01J 49/00* (2006.01)
(52) U.S. Cl.
USPC ........... 250/282; 250/281; 250/283; 250/287; 250/288

(58) Field of Classification Search
USPC .......................... 250/281, 282, 283, 287, 288
See application file for complete search history.

(56) References Cited

U.S. PATENT DOCUMENTS

| | | | |
|---|---|---|---|
| 2006/0014172 A1* | 1/2006 | Muller et al. ...................... 435/6 |
| 2009/0206245 A1* | 8/2009 | Nagahori et al. ............. 250/282 |
| 2010/0200742 A1* | 8/2010 | Schultz et al. ............. 250/252.1 |
| 2011/0014632 A1* | 1/2011 | Holzman et al. ................ 435/7.9 |
| 2011/0171749 A1* | 7/2011 | Alocilja et al. ............... 436/501 |

* cited by examiner

*Primary Examiner* — Michael Logie
(74) *Attorney, Agent, or Firm* — Global IP Services; Tianhua Gu

(57) ABSTRACT

Gene detecting methods without using PCR are disclosed. The methods comprise forming sandwich complexes by target genes with nano-probes and capture probes, wherein nano-probes are modified with recognition molecules and magnetic microparticles modified with capture molecules; then separating the sandwich complexes; releasing the nano-probes; and detecting molecular ion peaks of encoding molecules on the surface of nano-probes by mass spectrometric detection directly, characterized in that the proportions of recognition molecules and encoding molecules on the nano-probes are 300-2000:1.

15 Claims, 4 Drawing Sheets

SEQUENCE LISTING

<160> NUMBER OF SEQ ID NOS: 29

<210> SEQ ID NO 1
<211> LENGTH: 25
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 1
gcagtaccac aaggcaaaaa aaaaa                                         25

<210> SEQ ID NO 2
<211> LENGTH: 22
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 2
aaaaaaaaaa gcaccctatc ag                                            22

<210> SEQ ID NO 3
<211> LENGTH: 13
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 3
aaaaaaaaaa aaa                                                      13

<210> SEQ ID NO 4
<211> LENGTH: 27
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 4
gccttgtggt actgcctgat agggtgc                                       27

<210> SEQ ID NO 5
<211> LENGTH: 35
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 5
gctgtccctg taataaaccc gaaaattttt ttttt                              35

<210> SEQ ID NO 6
<211> LENGTH: 38
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 6
ctctgtggta ttgtgaggat tcttgtcatt tttttttt                    38

<210> SEQ ID NO 7
<211> LENGTH: 35
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 7
cgctttctgc gtgaagacag tagtttttttt ttttt                      35

<210> SEQ ID NO 8
<211> LENGTH: 36
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 8
gtgtactagc cctcccttct acctgatttt tttttt                      36

<210> SEQ ID NO 9
<211> LENGTH: 53
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 9
tttttttttt ttgtatgtct gttgctatta tgtctattat tctttcccct tgc   53

<210> SEQ ID NO 10
<211> LENGTH: 41
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 10
tttttttttt caaacgggca acataccttg gtagtccaga a                41

<210> SEQ ID NO 11
<211> LENGTH: 39
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 11
tttttttttt cgcaagcacc ctatcaggca gtaccacaa                   39

<210> SEQ ID NO 12
<211> LENGTH: 51
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 12
tttttttttt tttgtaatgt atcgtttgtt gcttctgtat ctatttcttg c     51

<210> SEQ ID NO 13
<211> LENGTH: 10
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 13
tttttttttt                                                          10

<210> SEQ ID NO 14
<211> LENGTH: 67
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 14
ttttcgggtt tattacaggg acagcgcagg ggaaagaata atagacataa tagcaacaga    60
catacaa                                                             67

<210> SEQ ID NO 15
<211> LENGTH: 59
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 15
tgacaagaat cctcacaata ccacagagtt ctggactacc aaggtatgtt gcccgtttg    59

<210> SEQ ID NO 16
<211> LENGTH: 54
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 16
aactactgtc ttcacgcaga aagcgttgtg gtactgcctg atagggtgct tgcg          54

<210> SEQ ID NO 17
<211> LENGTH: 67
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 17
tcaggtagaa gggagggcta gtacacgcaa gaaatagata cagaagcaac aaacgataca    60
ttacaaa                                                             67

<210> SEQ ID NO 18
<211> LENGTH: 44
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 18

```
cagggttggt aggtcgtaaa tcccctattg gtcaagagag acat                44
```

<210> SEQ ID NO 19
<211> LENGTH: 35
<212> TYPE: DNA
<213> ORGANISM: Artificial Sequence
<220> FEATURE:
<223> OTHER INFORMATION: mixed solution of bio-magnetic nanoprobes target DNA (HIV-1, HBV, HCV and TP).

<400> SEQUENCE: 19

```
gacaagaggt tggtgagtga ttggaggttg gggac                         35
```

<210> SEQ ID NO 20
<211> LENGTH: 37
<212> TYPE: DNA
<213> ORGANISM: Artificial Sequence
<220> FEATURE:
<223> OTHER INFORMATION: mixed solution of bio-magnetic nanoprobes target DNA (HIV-1, HBV, HCV and TP).

<400> SEQUENCE: 20

```
gaagattgac gatatgggtg aggcagtagt cggaaca                       37
```

<210> SEQ ID NO 21
<211> LENGTH: 32
<212> TYPE: DNA
<213> ORGANISM: Artificial Sequence
<220> FEATURE:
<223> OTHER INFORMATION: mixed solution of bio-magnetic nanoprobes target DNA (HIV-1, HBV, HCV and TP).

<400> SEQUENCE: 21

```
cctggaagta gaggacaaac gggcaacata cc                            32
```

<210> SEQ ID NO 22
<211> LENGTH: 22
<212> TYPE: DNA
<213> ORGANISM: Artificial Sequence
<220> FEATURE:
<223> OTHER INFORMATION: mixed solution of bio-magnetic nanoprobes target DNA (HIV-1, HBV, HCV and TP).

<400> SEQUENCE: 22

```
taacaataac caaaaaaaaa aa                                       22
```

<210> SEQ ID NO 23
<211> LENGTH: 27
<212> TYPE: DNA
<213> ORGANISM: Artificial Sequence
<220> FEATURE:
<223> OTHER INFORMATION: mixed solution of bio-magnetic nanoprobes target DNA (HIV-1, HBV, HCV and TP).

<400> SEQUENCE: 23

```
ggattattgt taaatattga taaggat                                  27
```

<210> SEQ ID NO 24
<211> LENGTH: 27
<212> TYPE: DNA
<213> ORGANISM: Artificial Sequence
<220> FEATURE:
<223> OTHER INFORMATION: mixed solution of bio-magnetic nanoprobes target DNA (HIV-1, HBV, HCV and TP).

<400> SEQUENCE: 24

```
ggataattgt taaatattga taaggat                                  27
```

```
<210> SEQ ID NO 25
<211> LENGTH: 27
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 25
ggattattgt taaatattga tagggat                                          27

<210> SEQ ID NO 26
<211> LENGTH: 25
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 26
aaaaaaaaaa atccttatca atatt                                            25

<210> SEQ ID NO 27
<211> LENGTH: 22
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 27
catactaaca taaaaaaaaa aa                                               22

<210> SEQ ID NO 28
<211> LENGTH: 27
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 28
tatgttagta tgatatagga atagtta                                          27

<210> SEQ ID NO 29
<211> LENGTH: 25
<212> TYPE: DNA
<213> ORGANISM: Artificial Sequence
<220> FEATURE:
<223> OTHER INFORMATION: mixed solution of bio-magnetic nanoprobes
      target DNA (HIV-1, HBV, HCV and TP).

<400> SEQUENCE: 29
aaaaaaaaaa taactattcc tatat                                            25
```

GENE DETECTING METHODS WITHOUT USING PCR

CROSS REFERENCE TO RELATED PATENT APPLICATION

The present application is the US national stage of PCT/CN2011/071044 filed on Feb. 17, 2011, which claims the priority of the Chinese patent application No. 201010147160.0 filed on Mar. 19, 2010, which application is incorporated herein by reference.

FIELD OF THE INVENTION

The present invention belongs to the field of molecular diagnostics, it provide and involves a gene detecting method without using PCR.

BACKGROUND OF THE INVENTION

Public health problem has always been a concern in the world. For example, hepatitis B virus and hepatitis C virus are the leading cause of morbidity of chronic hepatitis, and they directly lead to liver cancer. HIV causes AIDS infection, *treponema pallidum* causes sexually transmitted disease—syphilis, yet modern science and technology cannot control and treat these diseases well. In fact, whether the cancer or the infectious diseases, is one of the main threats to human health, this is mainly because of the lack of effective early diagnosis methods, corresponding preventive vaccines and effective drugs to treatment. Compared with the latter two, early diagnosis of disease may well be one of the most important means in the control of the development and dissemination of the diseases. From the perspective of prevention, laboratory diagnosis including traditional antigen-antibody reactions and the complex molecular biological diagnostic methods, these are all important effective methods for the diagnosis of diseases. Compared with the antigen-antibody detection, the molecular biological diagnosis based on biological macromolecules, mainly detects the genetic material of pathogenic (disease-causing) microorganisms—nucleotide, can shorten the window period of disease front several months to several days. The shortening of the window period is very important to the control of the spread of the diseases. Cur tend) the primary means of the detection of biomarkets in biological samples from infectious diseases (including nucleic acids and proteins), are enzyme linked immunosorbent assay (ELISA), polymerase chain reaction (PCR) products and probe hybridization with gel imaging etc, of which enzyme linked immunosorbent assay (ELISA) belong to the detection means based on antigen-antibody reactions. From the body infected with pathogenic microorganisms to the produce of antibodies will take several months or even longer time, and this is almost equivalent to the time of the window period of the disease. The others are a variety of detection methods derived from the PCR-based technology. Although there are many advantages of these methods which detect the target genes in the biological samples, and these methods are major supplementary means or reconfirm "gold standard" means of clinical antigen-antibody detection methods at present. There exist the shortcomings of "false positive", susceptible to pollution, high technical requirements, cumbersome and time-consuming etc. in these methods. These shortcomings are brought about by the PCR technology itself. Although these methods can detect at the molecular level, the rapid spread of infectious diseases made it a increasingly urgent need to address the problem to establish a low-cost, reliable, high sensitivity, high specificity, easy to operate, high-throughput DNA detection technology which can carry out diagnosis of a variety of diseases at the same time.

Nano-particles also known as ultrafine particles, generally refers to the particles in the size range from 1 to 100 nm, it is in the transition zone at the junction of atom clusters and macroscopic objects, and it is an excellent bio-molecular marker. The use of nano-probes which made from nano-materials in genetic testing methods, gradually attracts extensive attention in various fields of molecular diagnostics, etc., and increasingly demonstrates bright prospects for development.

In recent years, mass spectrometry (MS) technology has been developed, rapidly, and it has been widely used in the fields of chemical, petroleum, pharmaceutical, biotechnology, etc. it has become a very important tool in research and production. Especially the appearance of two "soft ionization" methods of matrix-assisted laser desorption ionization. (MALDI-TOF-MS, TOF MS) and electrospray ionization in the mid-1980s. with their characters of wide detection range, high sensitivity, easy to operate, high degree of automation and rapid detection, etc. they have been widely used in the study of biology, clinical medicine, environtology, etc. At present, German Qiagen Company has developed a set of technologies of encoding nucleic acids with organic molecules, and established a tag library of 64 encoded nucleic acid, which can simultaneously detect 22 pathogens with the use of mass spectrometry technology (Tgomas Briese et al. Diagnostic system for rapid and sensitive differential detection of pathogens. Emerging infectious diseases, 2005, 11(2), 310-313. Kokoris, Mark, et al. High-throughput SNP genotyping with the Masscode system. Molecular Diagnosis, 2000, 5(4), 329-340). This method binds the low molecular weight markers to nucleic acids with controllable optical switching technology, after PCR amplification, then conduct biometric identification, at last releases the markers by illumination and uses mass spectrometric detection to make judgments. This method designed very cleverly, but this method need bind the markers to biomolecules by chemical methods, and it need to release the markers again through chemical reactions before detection. This process is not only technically demanding, hut also cumbersome in operation and time-and-effort-consuming.

Patent CN101281164A disclosed an assembly method of mass-coded nano-probes, but the signal must be amplified by the PCR to read the detection sensitivity for the detection of the target. And it is not involved in the content of the practical applications, namely the durability test of this method of real biological samples. The specific process is: modify encoding molecules and corresponding recognition molecules to the surface of gold nano-particles, to make gold nano-probes. Bind gold nano-probes to target genes through hybridization, and then separate the nanoprobe-target complexes with treated silicon chip, at last detect the encoding molecules on the surface of colloidal gold-nanoprobes by mass spectrometric, thus the detection of target DNA can be achieved. Among which the encoding molecules are small organic molecules that can bind with gold nano-particles, and it can be detected by MS; and recognition molecules are DNA sequences that can carry out specific recognition reactions with target DNAs. The treated silicon chip has the role of capturing; gold-nano-probe-target-DNA complexes, this is because that the surface of the silicon chip was bound with another DNA sequence which can carry out specific recognition reactions with target DNA and this DNA sequence is different from recognition molecules. This kind of modified silicon chip only has separation and purification effect, without concentration effect of the targets. This method realized signal encoding and amplification by nano-probes, and without the need of releasing the encoding molecules from nano-probes, it can detect the encoding molecules directly. The mass spectrometric detection of encoding molecules has a high degree of automation. The maximum of its sensibility is up to $10^{-14}$M. But the biggest flaw of the present patent is that it still needs to amplify the target DNA by PCR. The target genes can be detected unless its concentration was raised. The whole operation process is tedious, time consuming. And its sensitivity cannot reach the level required by clinical testing.

SUMMARY OF THE INVENTION

The purpose of the present invention is, aims at the lacks of existing technology, to provide a kind of gene detecting method combined bio-magnetic nanoprobe with MS technology, which no longer need the PCR technology to amplify the signal of the target, to meet the clinical practical needs of the testing of biological samples, especially the needs of early diagnosis of disease.

The principles of the present invention are as follows: the bio-magnetic nanoprobes adopted in the present invention are composed of colloidal gold-nanoprobes and capture probes. The nano-probes are biomacromolecules which self-assembled on the surface of Au nanoparticles (AuNPs), they connected the recognition molecules which are used to recognize the target and the encoding molecules which are used to read and amplify signals. Capture probes are another kind of biomacromolecules (on the surface of the magnetic particles) which bound with recognizable target, it plays the roles of separation, purification and concentration in the targets existing environment. When bio-magnetic nanoprobes encountered with the targets, the sandwich complexes which consists of three parts: nano-probes, targets and capture probes, formed. Separate and purify these sandwich complexes, wash to remove the other interfering substances, detect the encoding molecules on the surface of the nano-probes by MS, to determine whether there is the targets in the tested samples or not.

The purpose of the present invention can be achieved by the following measures:

A kind of gene detecting method, comprise forming sandwich complexes by target genes with nano-probes and capture probes, wherein nano-probes are modified, with recognition molecules and magnetic microparticles modified with capture molecules; then separating the sandwich complexes; releasing the nano-probes; and detecting molecular ion peaks of encoding molecules on the surface of nano-probes by mass spectrometric detection directly, among which: the proportions of recognition molecules and encoding molecules on the nano-probes are 300-2000:1, and 1300-2000:1 are preferred.

The salt concentrations of the hybridization reaction system in which formed the sandwich complexes are 0.2~1.0 M and 0.5~0.7 M are preferred. In general, the salt is sodium chloride. Experimental results showed that the hybridization efficiency among DNA molecules rose with the raise of the salt concentrations of the system, and the stability of the system also rose. But too high salt concentration (the concentration exceeds 1 M) will inhibit the hybridization, and will result in nonspecific hybridization. The present study found that the salt concentration at 0.2~1.0 M, especially 0.5~0.7 M, can not only ensure a high hybridization efficiency, but also with no problem of nonspecific hybridization.

The MS is matrix-assisted laser desorption ionization time of flight mass spectrometry (MALDI TOF MS) or electrospray ionization mass spectrometry, and MALDI TOP MS is preferred. The matrix used in the MALDI TOF MS can be any kind of α-cyano-4-hydroxy cinnamic acid, 3,5-dimethoxy-4-hydroxy cinnamic acid, crude acid, 2,5-dihydroxybenzoic acid or the AuNPs self-assembled by DNA, and AuNPs self-assembled by DNA is preferred, especially the colloidal AuNPs self-assembled by the DNAs which are composed of 10-20 thymidines or adenines.

The MALDI TOF MS adopted Anchor ChipR4001384 target plate, nitrogen laser source with a wavelength of 337 nm to conduct the desorption and ionization of the test object.

The MALDI TOF MS adopted the mode of positive ion reflection, and detects under 10%~70% laser intensity, and 20%~50% laser intensity are preferred, especially 20%~35%.

The accelerating voltages adopted by the MALDI TOF MS are 20~35 KV and 25 KV is preferred.

The nano-materials of the nano-probes are gold nano-particles, with the particle sizes of 10~100 nm.

The encoding molecules are organic compounds with sulphydryl or disulfide bond in their molecules, and mercaptans, thioethers or bisulfides are preferred.

The magnetic microparticles can be inorganic microparticles, biopolymer microparticles or polymer microparticles, and polystyrene magnetic microparticles are preferred.

The surface of the magnetic microparticles is modified with amidogen or streptavidin.

The sandwich complexes can be separated by magnetic force frame.

The beneficial effects of the present invention:

The present invention is a gene detecting method which eliminated the need of PCR amplification. It mainly amplifies the signal of the target by raise the proportions of recognition molecules and encoding molecules on the surface of the colloidal gold-nanoprobes, and with the concentrate action of the modified magnetic microparticles, and modern analytical instruments of high sensitivity, thus achieved the gene detection of high specificity and high sensitivity with no longer need of the PCR technology to amplifies the target.

Patent application CN101281164A pointed a general direction of the detection of the genes or biological macromolecules with nano-probes and magnetic capture probes, wherein the nano-probes were modified by two molecules. But it did not stud the specific conditions which affect the sensitivity, so its sensitivity is not high. And it requires the help of PCR to amplify target genes when it is used for gene detection. The inventor studied the factors that affect the sensitivity through massive experiments on the basis of the former, determined the specific conditions, and improved the detection sensitivity significantly, namely the detection sensitivity raised from $10^{-14}$M to $10^{-17}$M. The present invention can detect biological macromolecules directly without PCR amplification, thus avoid the shortcomings of "false positive", susceptible to pollution, high technical requirements, cumbersome and time-consuming along with the PCR technology and eliminated the flaws of the enzymes required by the PCR process: expensive, easy to inactivation, difficult to preserve etc. The assembly process of the probes of the present invention is simple, with low technical requirements, and the probes can be produced in mass, and the stability of the probes is good, so the probes are easy to be stored. And the hybridization process is simple and rapid, easy to operate. And the degree of automation of MS analysis is high. All of these advantages are conducive to the clinical use of this method. The present invention provided a new thought of the early clinical diagnosis of the diseases.

Theoretically, we can use gene analysis to conduct very complicated multiplex assay with the organic molecules as mass barcodes. But current technology can only detect single- or double-target. Multiplex assay is a challenging problem for many analysis methods, this is because that the non-specific binding which may happen between the probes and non- targets, and the other various factors which must be considered in and required by the design of the probes, and the problem of the separation of the probe-target complexes from the analytes, and such problems which are very difficult and can not be avoided. All of these require not only high sensitivity, but also high specificity of the analysis methods. However, under normal circumstances, sensibility and specificity of the analysis methods is a pair of contradictions. According to actual needs of the methods, sometimes we must give up specificity to pursue high sensitivity, sometimes we must give up sensibility to pursue high specificity. The inventor greatly raised the proportions of recognition molecules and encoding molecules in the process of the self-assembly of the gold-nanoprobes through massive experiments, thus significantly unproved the detection sensitivity of the present invention; Based on this, the inventor adopted reaction system with high salt concentration, thus both improved the hybridization efficiency and eliminated nonspecific hybridization. And the inventor adopted colloid gold particles which were self-assembled by DNA (composed of 10-20 thymidines or adenines) as matrix in the detect process, thus there is almost no "background" which existed in other methods, and made the MS "Cleaner". All of these ensured both high sensitivity and high specificity of the gene detecting method, and provided powerful means to achieve multiplex assay of biological samples.

In this method, the detection of the targets was accomplished through the MS detection of molecular ion peaks of the encoding molecules which assembled on colloidal gold-nanoprobes. Theoretically, the greater the proportions of recognition molecules and encoding molecules, the better the signal amplification effect of the targets, the higher the sensibility. But, as the encoding molecules are liposoluble, its dissolution media is ethanol, too much ethanol in the assembly process will destroy the steady-state of the colloid gold, and cause its condensation and precipitation. Patent application CN101281164A just selected a proportion randomly from the references: it did not study the relationship of the proportions (of recognition molecules and encoding molecules) and the detection sensitivity, and the relationship of the proportions and stability of the probes. The present invention optimized the proportions (of recognition molecules and encoding molecules on the surface of the gold nano-particles) through massive parallel experiments on the basis of patent application CN101281164A. In the range of the proportions we determined, we can not only improve the sensibility, but also ensure the stability of the nano-probes. Out of the range of the proportions we determined, either sensitivity is too low, or probes failed in assembly.

Magnetic microparticle (MMP) is used in the present invention as solid support, it also has the rules of separation, purification and enrichment, it is also one of the main contributors which greatly improved the sensibility of the method. There are many types of the magnetic beads, they can be divided into inorganic microparticles, biopolymer microparticles and polymer microparticles etc., according to the materials from which the magnetic particles are made. The surface of the magnetic particles can bind with a variety of active groups. The magnetic particles used in the present invention, are a kind of microparticles with amidogen or streptavidin on their surface.

In summary, the method has many advantages, such as high sensitivity, high specificity, simple and rapid in operation, etc., it can be used in the direct detection of the targets in biological samples and the detection of multiplex targets, and it can also be used in the gene detection such as the detection of different types of single nucleotide polymorphism (SNP) in the genes and other aspects. In addition, with the help of double-labeled colloidal gold-nanoprobes, the method is especially effective in the detection of nucleotides of the same mass and different base sequences, which can not be distinguished by MS.

Parallel experiments were conducted three times for each concentration level respectively. The signal intensity in the figure was the result which has taken the dilution or concentration ratio and sample dose of the detect process into account.

Figure 5:
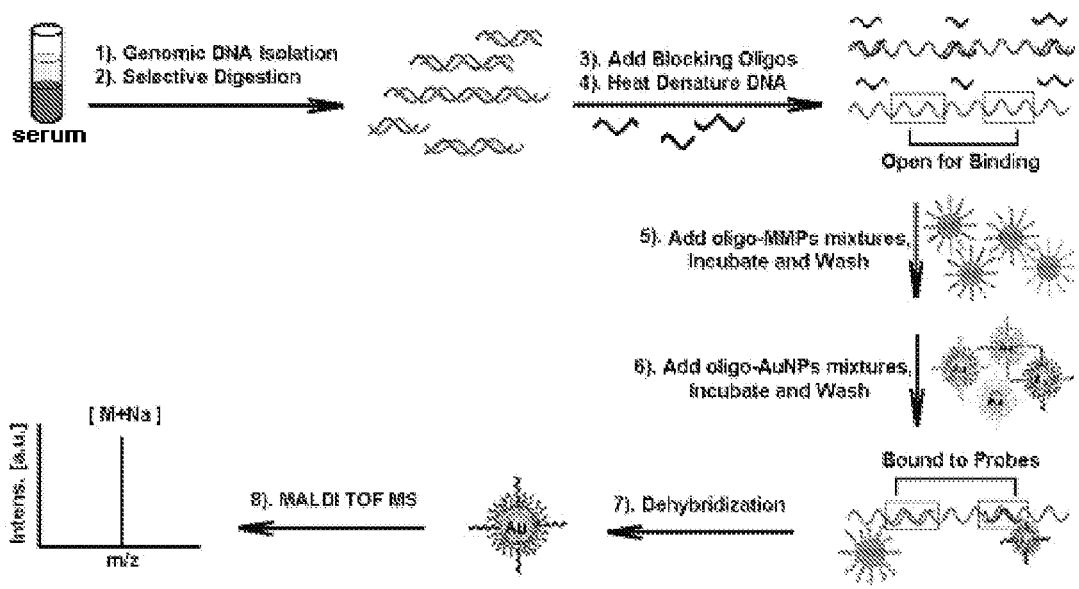

FIG. 5 The schematic diagram of the detect process of real biological samples.

Figure 6:
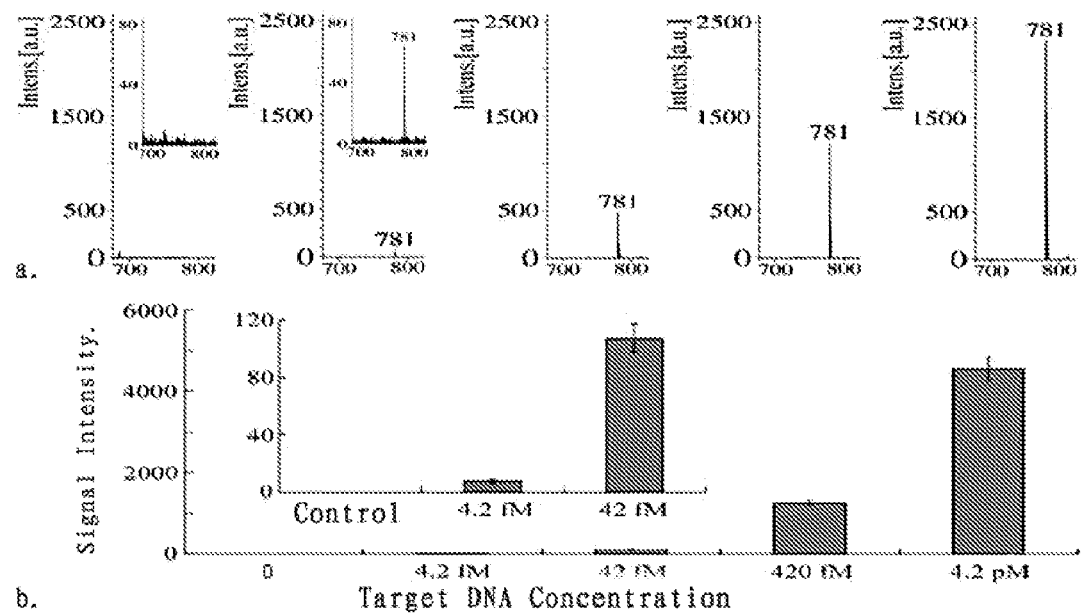

FIG. 6 The detection sensibility experiment of the target of real biological samples.

From left to right, a is the mass spectrum detection results of biological samples in which the target DNA concentration was 0, 4.2 fM, 42 fM, 420 fM and 4.2 pM in turn; b is the histogram of sensibility experiment respectively.

Figure 7:
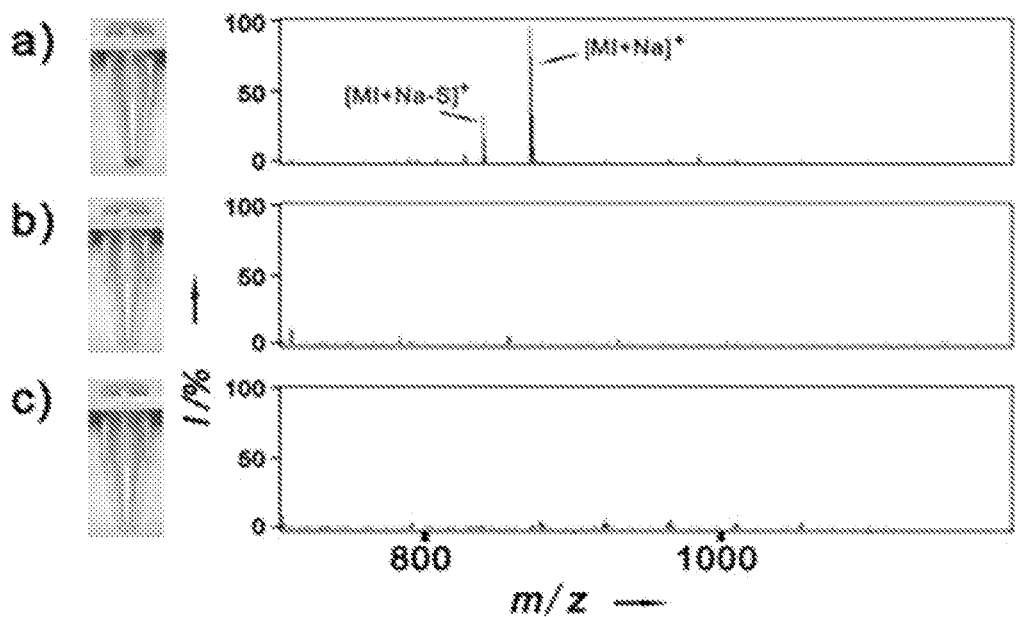

FIG. 7 The analysis of single nucleotide polymorphism (SNP)

a. The color of EP tube and the results of MS, of the reaction system in which target DNA) was added DNA1, capture probes and nano-probes, these three matched exactly, after the process of hybridization-dehybridization, the reaction system appeared red, and MS determined that there were peaks at m/z 869 ([M+Na]$^+$) and 837 ([M+Na—S]$^+$).

b. The color of EP tube and the results of MS, of the reaction system in which target DNA2 was added; As there was SNP in DNA2, thus DNA2 did not match with capture probes and nano-probes, the reaction system was colorless, and there's no peak demonstrated in MS detection.

c. The color of FP tube and the results of MS, of the reaction system in which target DNA3 was added; As there was SNP in DNA3, thus DNA3 did not match with capture probes and nano-probes, the reaction system was colorless, and there's no peak in MS detection.

Figure 8:
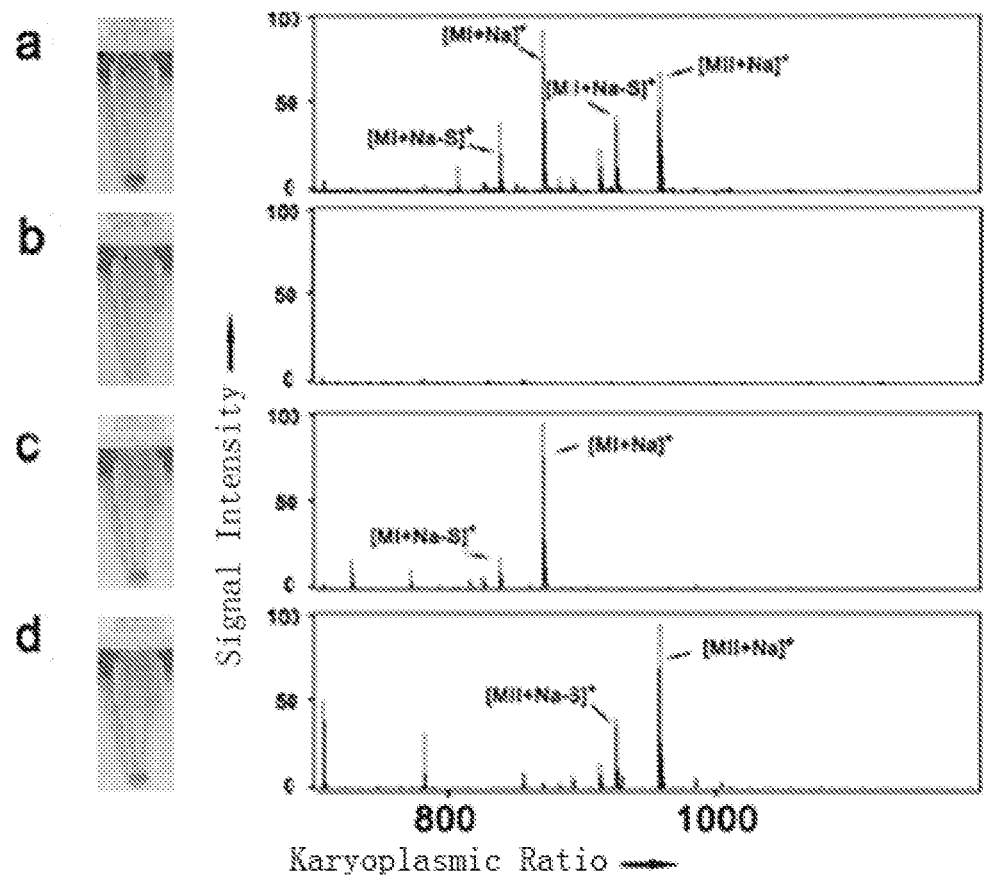

FIG. 8 The distinction of nucleotides of the same mass and different base sequences.

a The figure of the color reactions and MS detection results of the sample in which there were two target genes (DNA1 and DNA4);

b The figure of the color reactions and MS detection results of the sample in which there's no target gene at all;

c The figure of the color reactions and MS detection results of the sample in which there's DNA1 only;

d The figure of the color reactions and MS detection results of the sample in which there's DNA4 only.

DETAIL DESCRIPTION OF THE INVENTION

The synthesis and purification of all the DNAs used in the present invention were completed by Shanghai Invitrogen Corporation, Chloroauric acid (99.9%) was purchased from Shanghai Jiuyue Chemical Co., Ltd. SMPB was purchased from America Pierce Biotechnology Co., Ltd. The aminated magnetic microparticles were purchased from Shanghai Jiuyue Chemical Co., Ltd. Ultra-pure water was purified with Sartorius Arium 611 system. And we adopted Bruker MLtraflex III TOF/TOF Mass Spectrometer to conduct the MS detect throughout the whole experiment.

Embodiment 1

The Application of Bio-Magnetic Nanoprobes in the Detection of HCV-DNA (1) The preparation of HCV-AuNPs ① Took about 35 µg 1 OD HCV-DNA recognition molecules (5'GCA GTA CCA CAA GCC AAA AAA AAA A SH 3, SEQ ID NO. 1), centrifuged 5 minutes (5000 rpm), then dissolved with the add of 200 µL ultra-pure water, vortexed 30 seconds, mixed evenly;

② Added 2 mL of colloid gold (synthesized by ourselves, 13 nm, determined by transmission electron microscopy), kept shaking softly for 24 hours (20 rpm), at room temperature (25'C).

③ Added phosphoric acid buffer solution 1 (0.3M NaCl, 10 mM phosphoric acid buffer solution (PBS), pH=7.0), made the NaCl concentration of the system to 0.1 M, kept shaking softly and aging for 36 hours;

④ Added 48 µL pentaethylene glycol disulfate (with 100 mM ethanol as its dissolvent), kept shaking softly for 12 hours, and the colloidal gold-nanoprobes with the proportions of recognition molecules and encoding molecules of 1600:1 can be obtained. And store it at 4° C.

⑤ Before use, centrifuged 25 minutes (12,000 g), removed, the supernatant fluid, dispersed with phosphoric acid buffer solution 2 (0.1 M NaCl, 10 mM PBS, pH7.0), repeat (the centrifugal and wash) 3 times, and dispersed in phosphoric acid buffer solution 1 at last, its concentration was about 5 nM.

(2) The preparation of HCV Capture Probes (HCV-MMPs)

Washed the magnetic microparticles (Shanghai Invitrogen Corporation, 300 µL, 30 mg/ml) 3 times with 300 µL dimethyl sulfoxide (DMSO), and then dispersed in the SMPB (4-[p-maleimidophenyl]butyrate, succinimide) solution of DMS (1 mg/100 µL), vortexed 30 minutes, kept shaking 12 hours at room temperature, separated by magnetic force frame, and washed 3 times with 300 µL DMSC, then washed 2 times with 300 µL phosphoric acid buffer solution 3(0.15M NaCl, 0.1 M PBS, pH7.0).

Dissolved about 33 µg 1 OD HCV-DNA recognition molecules (5'SHA AAA AAA AAA GCA CCC TAT CAG 3' SEQ ID NO. 2) in 100 µL ultra—pure water, and put it into the above-mentioned aminated magnetic microparticles which was washed by DMSO, kept shaking 10 hours at room temperature, and wash 3 times with phosphoric, acid buffer solution 3; Then dispersed in phosphoric acid buffer solution 3, added 72 µM (1 OD) DNA (5'SHA AAA AAA AAA 3', SEQ ID NO. 3) which was passivated by 100 µL of A13, kept shaking 10 hours, washed 2 times with 300 µL phosphoric acid butler solution 4 (0.2 M NaCl, 10 mM PBS, pH7.2), and dispersed in 2 mL of phosphoric acid buffer solution 5 (0.3 M NaCl, 10 mM PBS, pH7.2).

(3) The Formation of the Sandwich Structure:

Add 30 µL of target HCV-DNA (5"-GCC TTG TGG TAC TGC CTG ATA GGG TGC 3', SEQ ID NO.4) into 50 µL of HCV-MMPs, and then added saturated sodium chloride phosphoric acid solution (prepared with phosphoric acid buffer solution 1, the concentration was about 6M, 25° C.), to make the sodium chloride concentration to be 0.6M, incubated with water bath for 30 minutes at 45° C., and shaked per 10 min, and then let it stand for 3 hours at room temperature, washed 3 times with phosphoric acid buffer solution 6 (0.65 M NaCl, 10 mM PBS, pH7.0), 100 µL/time, dispersed in 50 µL of phosphoric acid buffer solution 6 at last.

Added 50 µL of HCV-AuNPs, and then added the saturated sodium chloride phosphoric acid solution, to make the sodium chloride concentration of the system to be 0.62 M, let it stand for 3 hours at room temperature, and shaked per 10 minutes, then washed 7 times with phosphoric acid buffer solution 6, 200 µL/time, dispersed in 10 µL of ultra-pure water at last. Incubated with water bath for 5 minutes at 75° C., dehybridization, separated by magnetic force frame, detected with MS.

(4) MS Detection:

The detection with the self-assembled colloidal gold particles by 15 units of adenine (A15) as matrix, detect was easy to be conducted, and the MS was "Cleaner". The accelerating voltage of ion source 1 and Ion source 2 was 25 kV and 21.55 kV respectively, linear positive-ion scan mode, the accelerating voltage of the prism was 9.5 kV, the accelerating voltage of reflection component 1 and reflection component 2 was 26.3 kV and 13.85 kV respectively, the optimal laser intensity for the detection was 30% in general. Spotted 2 μL of the formation of dehybridization on the specific targen plate (Anchor-Chips, 400/385) for MALDITOF MS detection. Mainly detected sodium adduct ion peaks ([M+Na]$^+$) of encoding molecules. Detection limit can reach the level of 10 aM (10-17M), when the MS was used to detect target HCV-DNA.

Embodiment 2

Multiplex Assay Based on the Mixed Solution of Bio-Magnetic Nanoprobes Target DNA (HIV, HBV, HCV and TP)

The sequences of DNA strands involved in this embodiment were shown in table 1:

TABLE 1

| Sequence Name | Name | Sequence |
|---|---|---|
| SEQ ID NO. 5 | HIV-AuNP | 5'-GCT GTC CCT GTA ATA AAC CCG AAA ATT TTT TTT TT-(CH$_2$)$_3$-SH-3' |
| SEQ ID NO. 6 | HbV-AuNP | 5'-CTC TGT GGT ATT GTG AGG ATT CTT GTC ATT TTT TTT TT-(CH$_2$)$_3$-SH-3' |
| SEQ ID NO. 7 | HCV-AuNP | 5'-CGC TTT CTG CGT GAA GAC AGT AGT TTT TTT TTT TT-(CH$_2$)$_3$-SH-3' |
| SEQ ID NO. 8 | TP-AuNP | 5'-GTG TAC TAG CCC TCC CTT CTA CCT GAT TTT TTT TTT-(CH$_2$)$_3$-SH-3' |
| SEQ ID NO. 9 | HIV-MMP | 5'-SH-(CH$_2$)$_6$-TTT TTT TTT TTT GTA TGT CTG TTG CTA TTA TGT CTA TTA TTC TTT CCC CTG C-3' |
| SEQ ID NO. 10 | HBV-MMP | 5'-SH-(CH$_2$)$_6$-TTT TTT TTT TCA AAC GGG CAA CAT ACC TTG GTA GTC CAG AA-3' |
| SEQ ID NO. 11 | HCV-MMP | 5'-SH-(CH$_2$)$_6$-TTT TTT TTT TCG CAA GCA CCC TAT CAG GCA GTA CCA CAA-3' |
| SEQ ID NO. 12 | TP-MMP | 5'-SH-(CH$_2$)$_6$-TTT TTT TTT TTT TGT AAT GTA TCG TTT GTT GCT CTT GTA TCT ATT TCT TGC-3' |
| SEQ ID NO. 13 | Passivated DNA | 5'-SH-(CH$_2$)$_6$-TTTTTTTTTT-3' |
| SEQ ID NO. 14 | HIV-target | 5'-TTT TCG GGT TTA TTA CAG GGA CAG C-GCA GGG GAA AGA ATA ATA GAC ATA ATA GCA ACA GAC ATA CAA-3' |
| SEQ ID NO. 15 | HBV-target | 5'-TGA CAA GAA TCC TCA CAA TAC CAC AGA G TTC TGG ACT ACC AAG GTA TGT TGC CCG TTT G-3' |
| SEQ ID NO. 16 | HCV-target | 5'-AAC TAC TGT CTT CAC GCA GAA AGC G-TTG TGG TAC TGC CTG ATA GGG TGC TTG CG-3' |
| SEQ ID NO. 17 | TP-target | 5'-TCA GGT AGA AGG GAG GGC TAG TAC AC-GCA AGA AAT AGA TAC AGA AGC AAC AAA CGA TAC ATT ACA AA-3' |
| SEQ ID NO. 18 | HGV-DNA | 5'-CAG GGT TGG TAG GTC GTA AAT CC-CCT ATT GGT CAA GAG AGA CAT-3' |

Molecular formulas of small organic molecules are showed as follows:

M I: ($[S(CH_2)_{11}(OCH_2CH_2)_3OH]_2$, $[MI+Na]^+$ m/z 693
M II: ($[S(CH_2)_{11}(OCH_2CH_2)_4OH]_2$, $[MII+Na]^+$ m/z 781
M III: ($[S(CH_2)_{11}(OCH_2CH_2)_5OH]_2$, $[MIII+Na]^+$ m/z 869
M IV: ($[S(CH_2)_{11}(OCH_2CH_2)_6OH]_2$, $[MIV+Na]^+$ m/z 957

In this embodiment, the magnetic microparticles was polystyrene magnetic microparticles modified with amino on its surface, the preparation methods of capture probes and colloidal gold-nanoprobes were the same as these of embodiment 1, among which the sequences of SNP bound with the capture probes were shown in table 1, specifically, they are SEQ ID NO. 9, SEQ ID NO. 10, SEQ ID NO. 11 and SEQ ID NO. 12 respectively, and the sequences of SNP bound with the colloidal gold-nanoprobes were shown in table 1, specifically, they are SEQ ID NO. 5, SEQ ID NO. 6, SEQ ID NO. 7 and SEQ ID NO. 8 respectively.

Blended these two probes with phosphoric acid buffer solution 1 separately, and made the total concentration of the capture probes tube 16.0 mg/ml (contain four capture probes: HIV-MMP, HBV-MMP, HCV-MMP and TP-MMP, the concentrations of each of the probes were all 4.0 mg/mL), and made the total concentration of the gold-nanoprobes to be 500 pM (contain four gold-nanoprobes: HIV-AuNP, HBV-AuNP, HCV-AuNP and TP-AUNP, the concentrations of each of the probes were all 125 pM), the proportions of recognition molecules and encoding molecules on the surface of the gold-nanoprobes were all 1950:1).

Took 50 μL capture probes mixed solution, first added 100 μL saturated sodium (6M) chloride phosphoric acid solution (10 mM PBS, pH 7.0), then added 30 μpL test sample (among which the sequences of four target DNAs were shown in table 1, specifically, they are SEQ ID NO. 14, SEQ ID NO. 15, SEQ ID NO. 16 and SEQ ID NO. 17 respectively), incubated at 45° C. for 30 minutes, mixed 3 hours at 25° C. thus formed the capture-probes-target-DNA complexes, separated these complexes by magnetic force frame, washed 3 times with 200 μL phosphoric acid buffer solution 6, and then dispersed again in 50 μL of phosphoric acid buffer solution 6. Added 50 μL colloidal gold-nanoprobes mixed solution at the same time, hybridized at 25° C. overnight, thus formed the sandwich complexes, washed 7 times with phosphoric acid buffer solution 6, removed unbound nano-probes. And then dispersed the washed sandwich complexes again in 10 μL ultra-pure water, Heated at 70° C. to dehybridize, and finally conducted TOF MS detection of the formation of dehybridization.

Detection conditions of TOF MS are:

The accelerating, voltage of ion source 1 and ion source 2 was 25 kV and 21.55 kV respectively, the accelerating voltage of the prism is 9.5 kV, the accelerating voltage of reflection component 1 and reflection component 2 was 26.3 kV and 13.85 kV respectively, adopted linear positive-ion scan mode, the laser intensity was 30%. Spotting 0.1 μL-10 μL of the formation of dehybridization on the target plate (Anchor-Chips, 400/385) to conduct MALDI TOF MS detection. Detected sodium adduct ion peak ($[M+Na]^+$) of encoding molecules with the colloidal gold particles self-assembled by 20 units of thymidines (T20) as matrix.

2.1 Selected Experiment

Figure 1:
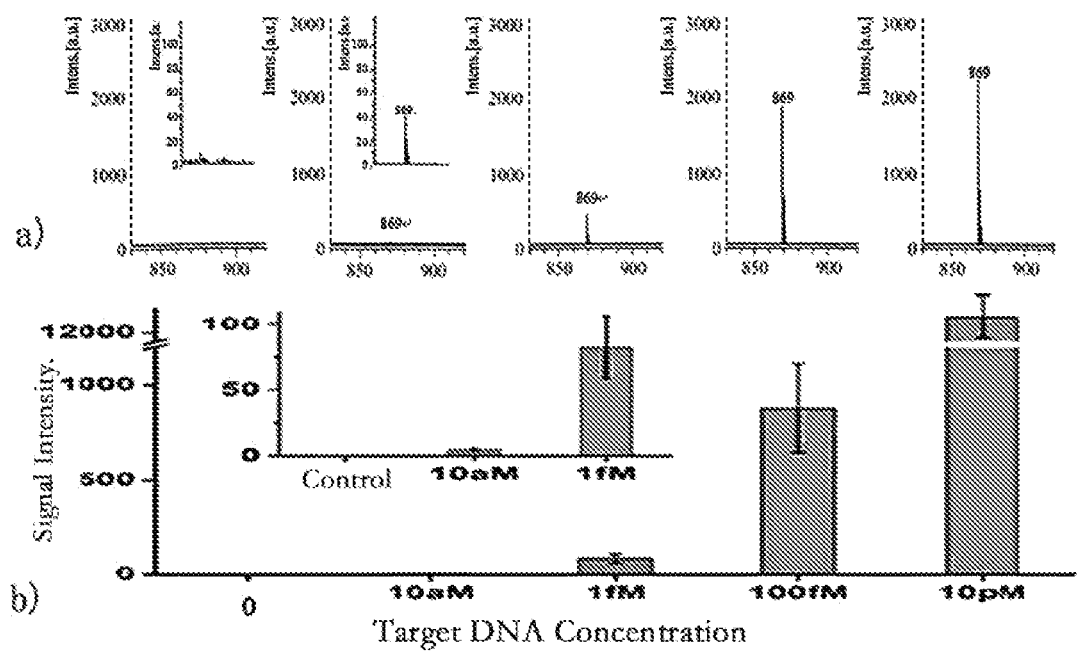
FIG. 1 The experimental results of the sensibility experiment of single target DNA detection.
 a. The spectrum of the TOP MS detection of the samples with the target DNA concentration is 0, $10^{-17}$, $10^{-15}$, $10^{-13}$, $10^{-11}$ M respectively, m/z869;
 b. The detection sensitivity histogram of the TOP MS of the samples with the target DNA concentration is 0, $10^{-17}$, $10^{-15}$, $10^{-13}$, $10^{-11}$ M respectively, the signal intensity in the figure was the result which has taken the dilution or concentration ratio and sample dose of the detect process into account.
Figure 2:
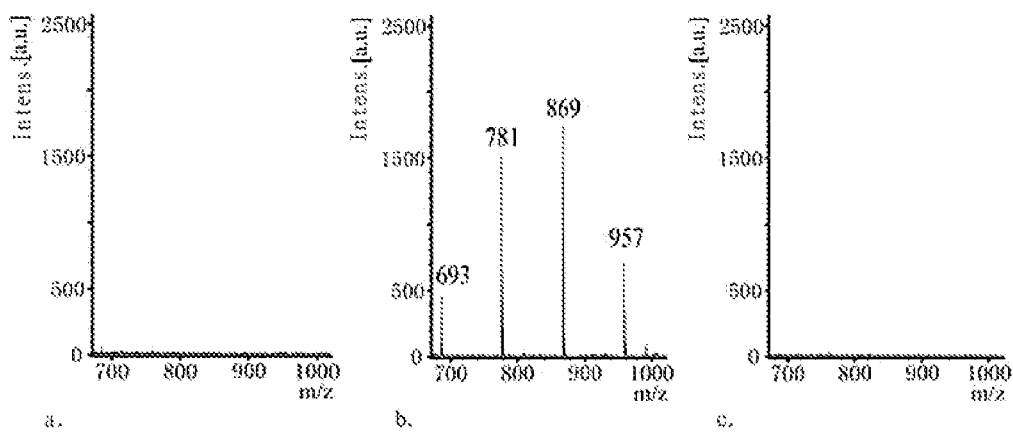
FIG. 2 The figure of the detection selectivity experimental results of multiple target genes.
 (A)
 a. Blank test, namely add 30 µL ultra-pure water in.
 b. Four kinds of sample solution of target DNAs (HIV-1, HCV, HBV and TP) was were added in the system, the total concentration was $10^{-10}$ M. and four peaks were demonstrated at m/z 693, 781, 869 and 957 respectively
 c. 30 µL sample solution which only has HGV (of which the DNA is completely mismatched) in it was added in the system, there's no peak demonstrated by the MS detection. This indicated that there's no formation of dehybridization.

The tested samples were the DNA mixed solution with the target DNA concentration (the total concentration of four target DNAs mixed solution included HCV HBV and TP) of 0, $10^{-10}$M, and HGV-DNA solution with the HGV-DNA (of which the DNA is completely mismatched, SEQ ID NO. 18) concentration of $10^{-10}$M. The other processes were the same as the processes described above, the results were shown in FIG. 2.

Figure 3:
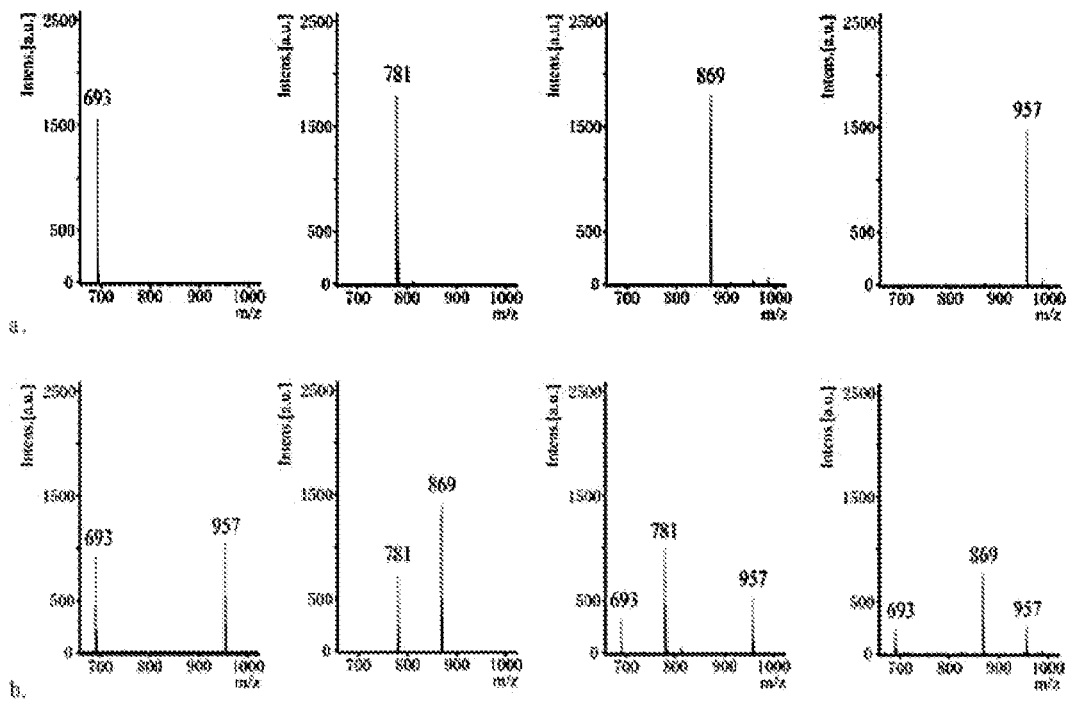
FIG. 3 The figure of the detection selectivity experimental results of multiple target genes.
 (B)
 From a to d, is mass spectrum of which 30 µL four kinds of target DNA (HIV-1, HBV, HCV and TP) sample solution were added in the system respectively, and corresponding peaks demonstrated at m/z 693, 781, 869 and 957 respectively; and e is mass spectrum of which two kinds of target DNA (HIV-1 and TP) sample solution were added in the system respectively, and corresponding, peaks demonstrated at m/z 693 and 957 respectively; and f is mass spectrum of which two kinds of target DNA (HCV and HBV) sample solution were added in the system respectively, and corresponding peaks demonstrated at m/z 781 and 869 respectively; and g is mass spectrum of which three kinds of target DNA HBV and TP) sample solution were added in the system respectively, and corresponding peaks demonstrated at m/z 693, 781 and
957 respectively, and h is mass spectrum of which three kinds of target DNA (HIV-1, HCV and TP) sample solution were added in the system respectively, and corresponding peaks demonstrated at m/z 693, 869 and 957 respectively.

The other processes were the same as above, the tested samples were mixed solutions contain 1, 2 and 3 target DNAs, the total concentration of these mixed solutions were all $10^{-10}$M. The results were shown in FIG. 3.

2.2 Sensitivity Determination

Figure 4:
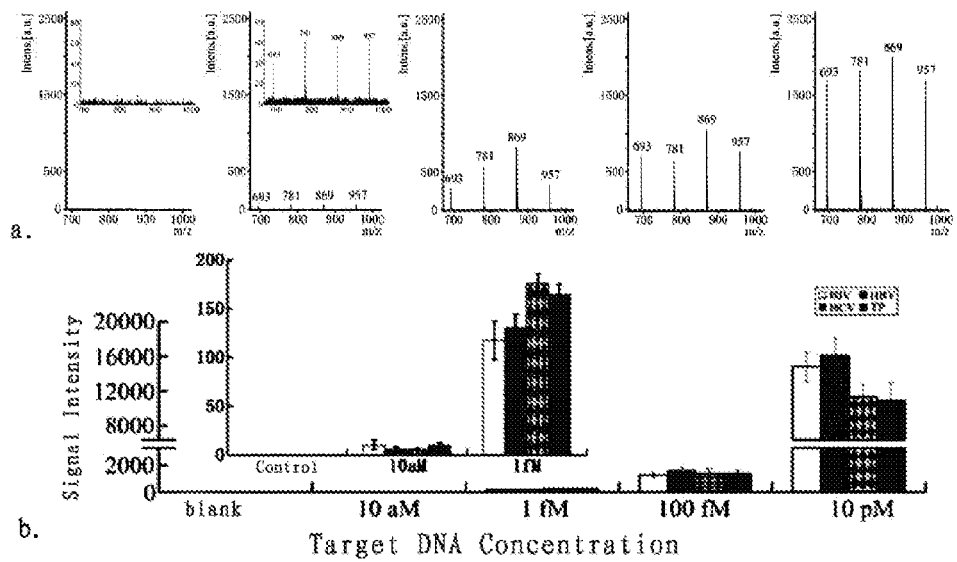
FIG. 4 The figure of the detection sensibility experimental results of multiple target genes From left to right, a is the mass spectrum of five kinds of sample solution (in which the total concentration of target DNA was 0, $10^{-17}$, $10^{-15}$, $10^{-13}$, $10^{-11}$ M respectively) in turn. b is the detection sensitivity histogram of the MALDI TOF MS of each sample solution (in which the total concentration of target DNA was 0, $10^{-17}$, $10^{-15}$, $10^{-13}$, $10^{-11}$ M respectively), The histogram of each concentration which arranged from the left to right, corresponds to HIV, HBV, HCV, TP gene respectively in turn.

The other processes were the same as above, the total target DNA concentration of these five samples was 0, $10^{-17}$, $10^{-15}$, $10^{-13}$, $10^{-11}$ M respectively, the results were shown in FIG. 4.

Embodiment 3

The Detection Biological Sample

HBV genome DNA is double-stranded covalently closed circular DNA. There have been reports showed that the key step of the detection of real biological samples is the use of inhibitory oligonucleotide chain (blocker) in the heat denaturation process of double-stranded DNA, to improve the hybridization efficiency of one of the single—chains and the probes. Because these inhibitory oligonucleotides can effectively prevent the renaturation of two single-stranded. DNAs during the cooling process, or prevent the formation of super-coiling structure of single-stranded DNA, so they can improve the hybridization efficiency of the probes. We adopted this method in this embodiment (see FIG. 5) to improve the hybridization efficiency, and multiplex assay of embodiment 2. And the detection limit of real biological samples can reach $10^{-15}$M.

3.1 The Detection of Biological Samples of Hepatitis B Patients

In this experiment the sequences of inhibitory oligonucleotide chains which can effectively prevent the renaturation and the formation of supercoiling structure, and improve the hybridization efficiency, are Center blocker: SEQ ID NO. 19, 5'-blocker: SEQ ID NO. 20, 3'-blocker: SEQ ID NO. 21 respectively.

The sequences and the preparation methods of the experiment in this part are exactly the same as these of four pairs of bio-magnetic nanoprobes used in the multiplex assay experiment in embodiment 2.

Experimental Process:

1) The Abstraction of HBV-DNA Genome:

DNA extraction kit (Shanghai Kehua Bio-Engineering Co., Ltd.), boiling method.

2) Digest HBV-DNA for Small Fragments, to Conduct Follow-Up Experiments:

Selected restriction endonuclease EcoN I (New England Biolabs), incubated at 37° C. overnight. And 879 bp HBV DNA fragments were obtained.

Enzyme digest react 20 μL system: 5 μL HBV-DNA, 2 μL 10× reaction buffer, 1 μL endonuclease (EcoN I, 15,000 U/mL), added 12 μL ultra—pure water.

3) Add Blocking DNA, and then Hybridize:

Add 3 kinds of block DNAs (1 μL/kind, with the concentration of 200 μM) into digested fragments equivalent to 10 μL HBV-DNA (equivalent to 4.2 fM, calculated from the results of real time fluorescence PCR), and then add 27 μL buffer 7 (0.15 M NaCl, 10 mM PBS, pH7.4), Denaturalized at 95° C. for 15 minutes, renatured overnight at 72° C. Then rapidly add 10 μL mixed solution of capture probes (20 mg/mL) and 4.5 μL saturated sodium (6M) chloride phosphoric, acid solution (10 mM PBS, pH 7.0), drop the temperature to 25° C. and mix for 4 hours, during which keep mixing gently, thus formed the capture-probes-target-DNA complexes, separated these complexes by magnetic force frame, wash 3 times with 200 μL phosphoric acid buffer solution 6, and then disperse in 50 μL of phosphoric, acid buffer solution 6 again, add 50 μL mixed solution of gold-nanoprobes (500 pM), hybridized overnight at 25° C., thus formed the sandwich complexes, wash 7 times with phosphoric acid buffer solution 6, remove unbound nano-probes. Then washed the sandwich complexes and dispersed it again in 10 μL ultra-pure water. dehybridized at 70° C. by heat, separate by magnetic force frame, conduct MALDI TOF MS detection of the formation of dehybridization, detection conditions were the same as these of embodiment 2, spot 0.1 μL~5 μL of the formation of dehybridization on the targen (Anchor-Chips, 400/385) for MALDI TOF MS detection. Detected sodium adduct ion peak ([M+Na]$^+$) of encoding molecules, with the self-assembled colloidal gold particles by 20 units of thymidines (T20) as matrix.

3.2 The Experiment of Detection Sensibility of the Biological Samples

Took the digested products equivalent to the target DNA concentration of 0, 4.2, 42, 420 fM and 4.2 pM, and operate it by steps 3.1, determine the detection limit, the results were shown in FIG. 6.

Table 2 Embodiment 4 the Detection of Single Nucleotide Polymorphism DNA (SNP Detection)

The sequences of DNA strands involved in this embodiment are shown in Table 2.

(5'-HS(CH2)6-AAAAAAAAAA ATC CTT ATC AAT ATT-3', SEQ ID NO. 26) and 50 μL colloidal gold-nanoprobes dual-modified by encoding molecules MIII ([S(CH2)11 (OCH2CH2)5OH]2, [MI+Na]$^+$ m/z 869, the mole ratio of encoding molecules and recognition molecules is 350:1), after the hybridization of 2 hours, this formed the sandwich complexes or captured probes, wash them 7 times with phosphoric acid buffer solution 1, remove unbound colloidal gold-nanoprobes and then dispersed the washed sandwich complexes or capture probes again in 10 μL phosphoric acid buffer solution 1. Incubate at 75° C. for 5 minutes, separate by magnetic force frame, spot on target, conduct MS detection, detection conditions are the same as these of embodiment 2, the optimal laser intensity is 10%. Spot 2 μL of the formation of dehybridization on the targen (Anchor-Chip^ 400/385) for MALDI TOF MS detection. Detected sodium adduct ion peak ([M+Na]$^+$) of encoding molecules, with the self-assembled colloidal gold particles by 10 units of thymidines (T10) as matrix.

The results showed that in the reaction system in which the DNA1 is added, DNA1 matched exactly with capture probes, and formed sandwich complexes, after dehybridization, the system appeared red; MALDITOF MS was adopted to conduct the detection, encoding molecules showed the exist of

TABLE 2

| Sequence Name Name | Sequence |
|---|---|
| SEQ ID NO. 22 DNAII-MMP | 5'-TAA CAA TAA CCA AAA AAA AAA A-(CH$_2$)$_3$SH-3' |
| SEQ ID NO. 23 DNA1-target | 5' GGA TTA TTG TTA AAT ATT GAT AAG GAT 3' |
| SEQ ID NO. 24 DNA2-target | 5' GGA TAA TTG TTA AAT ATT GAT AAG GAT 3' |
| SEQ ID NO. 25 DNA3-target | 5' GGA TTA TTG TTA AAT ATT GAT AGG GAT 3' |
| SEQ ID NO. 26 DNA1-AUNP | 5'-HS(CH$_2$)$_6$-A AAA AAA AAA ATC CTT ATC AAT ATT-3' |

Modify polystyrene magnetic microparticles (of which there's amido on its surface) with DNAII (5'-TAA CAA TAA CCA AAA AAA AAA A-(CH2)3SH-3', SEQ ID NO. 22) to form capture probes. Add capture probes (of which the concentration is 4.5 mg/mL) and target DNA1 (SEQ ID NO. 23, which matched exactly with capture probes), target DNA2 with single nucleotide mutation (SEQ ID NO. 24, of which there is a single nucleotide mutation of T to G at the fifth base from the 5' end, the other base sequences are the same as DNA1) and target DNA3 (SEQ ID NO. 25, of which there is a mutation of A to G at the fifth base from the 3' end, the other base sequences are the same as DNA1), the concentrations of each of the target DNAs are all 10 nM, incubate at 45° C. for 30 minutes, mix at 25° C. for 2 hours. Thus formed the capture-probes-target-DNA complexes or capture probes, are separated by magnetic force frame, washed 3 times with 200 μL phosphoric acid buffer solution 1, and then disperse again in 50 μL of phosphoric acid buffer solution 1. Add DNA1 exact match DNA1 (m/z 869 ([M+Na]$^+$) and 837 ([M+Na—S]$^+$)). See FIG. 7*a*. When as in the system in which the DNA2 and DNA3 was added, because of the exist of a SNP, DNA2 and DNA3 did not match with capture probes, thus they could not form sandwich complexes, the system appear colorless; MALDITOF MS was adopted to conduct the detection, there were no MS signal pea. See FIGS. 7*b* and 7*c*.

Embodiment 5

The Distinction of DNA Fragments of the Same Mass and Different Base Sequences

The sequences of DNA strand involved in this embodiment were shown in table 3,

TABLE 3

| Sequence Name | Name | Sequence |
|---|---|---|
| SEQ ID NO. 22 | DNAII-MMP | 5'-TAA CAA TAA CCA AAA AAA AAA A-(CH$_2$)$_3$SH-3' |
| SEQ ID NO. 23 | DNA1-target | 5' GGA TTA TTG TTA AAT ATT GAT AAG GAT 3' |
| SEQ ID NO. 26 | DNAI-AUNP | 5'-HS(CH$_2$)$_6$-A AAA AAA AAA ATC CTT ATC AAT ATT-3' |
| SEQ ID NO. 27 | DNAII'-MMP | 5'-CAT ACT AAC ATA AAA AAAAAA A-(CH$_2$)$_3$SH-3' |
| SEQ ID NO. 28 | DNA4-target | 5' TAT GTT AGT ATG ATA TAG GAA TAG TTA 3' |
| SEQ ID NO. 29 | DNAI'-AuNP | 5'-HS(CH$_2$)$_6$-A AAA AAA AAA TAA CTA TTC CTA TAT-3' |

The encoding small molecules involved in this embodiment are as follow:
M III: ([S(CH$_2$)$_{11}$(OCH$_2$CH$_2$)$_5$OH]$_2$, [MI+Na]$^+$ m/z 869
M IV: ([S(CH$_2$)$_{11}$(OCH$_2$CH$_2$)$_6$OH]$_2$, [MII+Na]$^+$ m/z 957

MS detection cannot distinguish DNA fragments of the same mass and different base sequences. But now the methods disclosed in the present invention can solve this problem, we selected 2 target DNA strands—DNA1 and DNA4 (their sequences are shown in Table. 3, and their sequence sames are SEQ ED NO. 23 and SEQ ID NO. 28). They have the same mass, but the different base sequences. Two pairs of biomagnetic nanoprobes, sodium adduct ion peaks corresponding to encoding molecules are m/z 837&869 and m/z 925 & 957, the specific process is as follows:

Modify two capture probes with DNAII and DNAII' respectively, and then hybridize with four solutions respectively in phosphoric acid buffer solution 1, four solutions are as follows: target DNA mixed solution contain both DNA1 and DNA4, solution without target DNA (water, as blank/control experiment), target DNA solution contain only DNA1 and target DNA solution contain only DNA4, incubate at 45° C. for 30 minutes, mix at 25° C. for 3 hours. Thus formed the capture-probes-target-DNA complexes or capture probes, are separated by magnetic force frame, wash 3 times with 200 μL phosphoric acid buffer solution 1, and then disperse again in 50 μL of phosphoric acid buffer solution 1. Add 50 μL mixed solution of gold-nanoprobes double-labeled with encoding molecules MIII and recognition molecules DNAI (SEQ ID NO. 26) & gold-nanoprobes double-labeled with MIV and recognition molecules DNA1' (in which the mole ratio of encoding molecules and DNA strands is 1000:1 respectively), hybridize 2 hours, hus formed the sandwich complexes, wash the sandwich complexes 7 times with phosphoric acid buffer solution 1 at 38° C., remove unbound colloidal gold-nanoprobes, then disperse the washed complexes again in 10 μL phosphoric, acid buffer solution 1. Incubate at 75° C. for 5 minutes, separated by magnetic force frame, spot on target, conduct MS detection. Detection conditions are the same as these of embodiment 2, the laser intensity is 20%. Spot 2 μL of the formation of dehybridization on the targen (Anchor-Chips 400/385) for MALDI TOF MS detection. Detected sodium adduct ion peak ([M+Na]$^+$) of encoding molecules with the self-assembled colloidal gold particles by 20 units of thymidines (T20) as matrix. The experimental results are shown in table 8.

To ensure that the experiment been carried out accurately and flawlessly, we selected high target DNA concentration of 10 nM leve, thus we can make a preliminary judgment on the experimental results by the change of the color, and then conduct the MS detection of related DNA1 and DNA4. The results showed that when two target DNAs of the same mass and different base sequences exist simultaneously, the reaction system appear red, and two encoding molecules cm be detected at the same time in MS detection, see FIG. 5a. This result showed that, in target DNA1 and DNA4, there exist simultaneously in the tested solution, that disclosed that different DNAs of the same mass and different base sequences can be distinguished by the present method. When there were none of these two target DNAs, namely added ultra—pure water as the blank control, system solution appeared colorless, and MS detected none of the encoding molecules, see FIG. 8b.

When target DNA solutions which contain only DNA1 or DNA4 were added, the system appeared red both, and MS detection can only detect: corresponding encoding molecules respectively, see FIGS. 8c and 8d.

Experimental results also showed at the same time, that even conduct this hybridization experiment of the bio-magnetic nanoprobes under the concentration of 10 nM which is much higher than the detection limit, no interferences of nonspecific hybridization were observed.

Embodiment 6

Optimization Experiments of the Proportions of Recognition Molecules and Encoding Molecules on the Surface of 1.3-mn Colloidal Gold-Nanoprobes (1) The Preparation of Nano-Probes (AuNPs):
① Took 33 μg of the recognition molecules of 1 OD HCV-DNA (5'-GCA GTA CCA CAA GGC AAA AAA AAA A-(CH2)3-SH-3', SEQ ID NO.1), centrifuged for 5 minutes (5000 rpm), then dissolved with the add of 200 μL ultra-pure water, vortexed for 30 seconds, mixed evenly;
② Added 2 mL of colloid gold (synthesized by ourselves, 13 nm, and determined by electron microscopy), kept shaking softly for 24 hours (20 rpm), at room temperature (25° C.).
③ Added phosphoric acid buffer solution 1 (0.3M NaCl, 10 mM PBS, pH=7.0), to make the NaCl concentration oldie system to 0.1 M, kept shaking softly for the aging for 36 hours;
④ Added dithio-pentaethylene glycol of amounts showed in Table. 4 according to its proportion, kept shaking softly for 12 hours, and the nano-probes assembled by recognition molecules and encoding molecules of the corresponding proportions can be obtained. And store it at 4° C.
⑤ Before use, centrifuged 25 minutes, removed the supernatant fluid, dispersed with phosphoric acid buffer solution 1 (0.1M NaCl, 10 mM PBS, pH7.0), repeat the centrifugal and wash 3 times, and dispersed in phosphoric acid buffer solution I at last, its concentration was about 5 nM.

(2) The Preparation of Capture Probes (MMPs):

Washed the laminated magnetic micro particles (Shanghai Nitrogen Corporation, 300 μL, 30 mg/ml) 3 times with 300 μL Diethyl sulfoxide (DMSO), and then dispersed in the SMPB (4-[p-maleimidophenyl]butyrate, succinimide) solution of DMSO (1 mg/100 μL), vortexed 30 minutes, kept shaking 12 hours at room temperature, separated by magnetic forte frame, and washed 3 times with 300 μL DMSC, then washed 2 times with 300 μL phosphoric acid buffer solution 3 (0.15M NaCl, 0.1 M PBS, pH17.0).

Dissolved about 33 μg 1 OD HCV-DNA recognition molecules (5'-$(CH_2)_6$-SHA AAA AAA AAA GCA CCC TAT CAG 33', SEQ ID NO.2) in 100 μL ultra-pure water, and put it into the above-mentioned aminated magnetic beads which was washed by DMSO, kept shaking 10 hours at room temperature, and wash 3 times with phosphoric acid buffer solution 3; Then dispersed in phosphoric acid buffer solution 3, added 100 μL, 72 μM passivated DNA (5'-$(CH_2)_6$-SHAAAAAAAAAA-3', SEQ ID NO.3), kept shaking 10 hours, washed 2 times with 300 μL phosphoric acid buffer solution 4 (0.2M NaCl, 10 mM PBS, pH7.2), and dispersed in 2 mL of phosphoric acid buffer solution 5 (0.3M NaCl, 10 mM PBS, pH7.2)

(3) The Formation of the Sandwich Structure:

Add 30 μL of target HCV-DNA (5'-GCC TTG TGG TAC TGC CTG ATA GGG TGC-3', SEQ ID NO. 4) into 50 μL of HCV-MMPs, and then added saturated sodium chloride phosphoric acid solution (prepared with phosphoric acid buffer solution 1, the concentration was about 6M, 25° C.), to make the sodium chloride concentration of 0.6M, incubated with water bath for 30 minutes at 45° C., and shaked per 10 minutes, and then let it stand for 3 hours at room temperature, washed 3 times with phosphoric acid buffer solution 1, 100 μL/time, dispersed in 50 μL of phosphoric acid buffer solution 1 at last. Added 50 μL of HCV-AuNPs with different assembly proportion of two substances on the surface of the nano-probes, and then added the saturated sodium chloride phosphoric acid solution, to make the sodium chloride concentration of the system to be 0.62 M, let it stand for 3 hours at room temperature, and slaked, per 30 minutes, then washed 7 times with phosphoric acid buffer solution 6 (0.65M NaCl, 10 mMPBS, pH7.0), 200 μL/time, dispersed in 10 μL of ultra-pure water at last. Water bath 5 minutes at 75'C, unspooled, separated by mimetic force frame, and detected with MS.

(4) MS Detection:

The detection with the self-assembled colloidal gold by 20 units of adenine (A20) as matrix, is easy to be determined, and the MS is "Cleaner". The accelerating voltage of ion source 1 and Ion source 2 was 25 kV and 21.55 kV respectively, linear positive-ion scan mode, the accelerating voltage of the prism was 9.5 kV, the accelerating voltage of reflection component 1 and reflection component 2 was 26.3 kV and 13.85 kV respectively, the optimal laser intensity is 30% in general. Spot 2 μL of the formation of dehybridization on the targen (Anchor-Chips 400/385) for MALDI TOF MS detection. Mainly detected molecular ion peaks [M+Na]$^+$.

The relationship of the detection sensitivity of the detection method and the proportions of recognition molecules and encoding molecules is that: With the proportions of recognition molecules and encoding molecules ranged from 1300:1 to 2000:1, detection limit reached the level of 10 aM (10-17M), Out of this range: sensibility declined with the decrescence of the proportions of these two; and sensibility also declined with the increase of the proportions of these two, until the amount of encoding molecules added caused the failure of nano-probes assembly. Namely, with proportions of the mass labeled molecules and DNA molecules increased gradually, the nano-probes assembled are used in the sensibility detection of the method, the whole trend the familiar bell-shaped curve, the results are showed in Table. 5

TABLE 4

| Serial number | The proportions of encoding molecules and recognition molecules concentration | The dosage of encoding molecules (μl) | The dosage of recognition molecules (μl) |
|---|---|---|---|
| 1$^a$ | 150:1 | 45 | 3.0 nmol |
| 2$^a$ | 200:1 | 60 | 3.0 nmol |
| 3$^a$ | 250:1 | 75 | 3.0 nmol |
| 4$^a$ | 350:1 | 105 | 3.0 nmol |
| 5$^b$ | 500:1 | 30 | 3.0 nmol |
| 6$^b$ | 800:1 | 50 | 3.0 nmol |
| 7$^b$ | 1000:1 | 60 | 3.0 nmol |
| 8$^b$ | 1300:1 | 80 | 3.0 nmol |
| 9$^b$ | 1700:1 | 100 | 3.0 nmol |
| 10$^c$ | 2000:1 | 60 | 3.0 nmol |
| 11$^c$ | 2300:1 | 70 | 3.0 nmol |
| 12$^c$ | 2700:1 | 80 | 3.0 nmol |
| 13$^c$ | 3000:1 | 90 | 3.0 nmol |
| 14$^c$ | 3300:1 | 100 | 3.0 nmol |
| 15$^c$ | 3700:1 | 110 | 3.0 nmol |

In Table.1, a: means that the concentration of dithio-pentaethylene glycol added is 10 mM; b: means that the concentration of dithio-pentaethylene glycol added is 50 mM; c: means that the concentration of dithio-pentaethylene glycol added is 100 mM;

TABLE 5

| Serial number | The proportions of encoding molecules and recognition molecules concentration | TARGET DNA CONCENTRATION (M) | | | | | |
|---|---|---|---|---|---|---|---|
| | | $10^{-9}$ | $10^{-11}$ | $10^{-13}$ | $10^{-15}$ | $10^{-17}$ | $10^{-18}$ |
| 1 | 150:1 | + | − | − | − | − | − |
| 2 | 200:1 | + | + | − | − | − | − |
| 3 | 250:1 | + | + | − | − | − | − |
| 4 | 350:1 | + | + | + | − | − | − |
| 5 | 500:1 | + | + | + | − | − | − |
| 6 | 800:1 | + | + | + | + | − | − |
| 7 | 1000:1 | + | + | + | + | − | − |
| 8 | 1300:1 | + | + | + | + | + | − |
| 9 | 1700:1 | + | + | + | + | + | − |
| 10 | 2000:1 | + | + | + | + | + | − |
| 11 | 2300:1 | + | + | + | − | − | − |
| 12 | 2700:1 | + | + | − | − | − | − |
| 13 | 3000:1 | + | + | − | − | − | − |
| 14 | 3300:1 | + | − | − | − | − | − |
| 15 | 3700:1 | Probes assembly failed | | | | | |

+: Encoding small molecular can be detected by MALDI TOF MS, the peak of m/z 869 appeared in mass spectrum.
−: No peak appeared in mass spectrum.

What is claimed is:

1. A gene detecting method comprising:
    forming sandwich complexes by target genes with nano-probes and capture probes, wherein the nano-probes are modified with recognition molecules and magnetic microparticles modified with capture molecules; then
    separating the sandwich complexes;
    releasing the nano-probes; and
    detecting molecular ion peaks of encoding molecules attached on surface of the nano-probes by mass spectrometric detection directly;
    wherein a proportions of the recognition molecules and the encoding molecules on the nano-probes are 300-2000:1;
    wherein a salt concentrations of a hybridization reaction system in which the sandwich complexes being formed are 0.2~1.0M.

2. The gene detecting method as claimed in claim 1, characterized in that a salt concentration of the hybridization reaction system in which the sandwich complexes being formed is 0.5~0.7M.

3. The gene detecting method as claimed in claim 1, characterized in that the mass spectrometry is a matrix-assisted laser desorption ionization time of flight mass spectrometry or an electrospray ionization mass spectrometry.

4. The gene detecting method as claimed in claim 3, characterized in that a matrix used in the matrix-assisted laser desorption ionization time of flight mass spectrometry is any one of α-cyano-4-hydroxy cinnamic acid, 3,5-diethoxy-4-hydroxy cinnamic acid, erucic acid, 2,5-dihydroxybenzoic acid or the Au nanoparticles self-assemblied by DNA.

5. The gene detecting method as claimed in claim 4, characterized in that the matrix used in the matrix-assisted laser desorption ionization time of flight mass spectrometry is colloidal Au nanoparticles self-assembled by DNAs composed of 10~20 thymidines or adenines.

6. The gene detecting method as claimed in claim 3, characterized in that the matrix-assisted laser desorption ionization time of flight mass spectrometry adopts a positive ion reflection mode, and detects under 10%~70% laser intensity.

7. The gene detecting method as claimed in claim 3, characterized in that the mass spectrometry is matrix-assisted laser desorption ionization time of flight mass spectrometry.

8. The gene detecting method as claimed in claim 1, characterized in that the nano-particles are Au nano-particles, with the particle size of 1~100 nm.

9. The gene detecting method as claimed in claim 1, characterized in that the encoding molecules are organic compounds with sulphydryl or disulfide bond in their molecules.

10. The gene detecting method as claimed in claim 9, characterized in that the encoding molecules are mercaptans, thioethers or bisulfides.

11. The gene detecting method as claimed in claim 1, characterized in that the magnetic microparticles are inorganic microparticles, biopolymer microparticles or polymer microparticles.

12. The gene detecting method as claimed in claim 11, characterized in that the magnetic microparticles are polystyrene magnetic microparticles.

13. The gene detecting method as claimed in claim 1, characterized in that the surfaces of the magnetic microparticles are modified with amidogen or streptavidin.

14. The gene detecting method as claimed in claim 11, characterized in that the surfaces of the magnetic microparticles are modified with amidogen or streptavidin.

15. The gene detecting method as claimed in claim 1, characterized in that the proportions of recognition molecules and encoding molecules on the nano-probes are 1300-2000:1.

* * * * *